(12) United States Patent
Ropiak et al.

(10) Patent No.: US 7,921,594 B2
(45) Date of Patent: Apr. 12, 2011

(54) METHODS FOR TESTING INSECT CONTROL PRODUCTS

(75) Inventors: Daniel T. Ropiak, Kenosha, WI (US);
Gopal P. Ananth, Racine, WI (US); Joel E. Adair, Racine, WI (US); Dirk K. Nickel, Mukwonago, WI (US);
Sebastian D. Hasik, Antioch, IL (US)

(73) Assignee: S.C. Johnson & Son, Inc., Racine, WI (US)

( * ) Notice: Subject to any disclaimer, the term of this patent is extended or adjusted under 35 U.S.C. 154(b) by 419 days.

(21) Appl. No.: 12/032,834

(22) Filed: Feb. 18, 2008

(65) Prior Publication Data

US 2008/0257075 A1  Oct. 23, 2008

Related U.S. Application Data

(60) Provisional application No. 60/913,333, filed on Apr. 23, 2007.

(51) Int. Cl.
*A01M 1/02* (2006.01)
*A01M 1/06* (2006.01)
*A01M 1/10* (2006.01)

(52) U.S. Cl. ............... 43/122; 43/107; 43/111; 43/114

(58) Field of Classification Search ............... 73/28.01, 73/31.01–31.03, 863.41, 863.42; 43/107–123
See application file for complete search history.

(56) References Cited

U.S. PATENT DOCUMENTS

| | | | |
|---|---|---|---|
| 1,701,674 A * | 2/1929 | Hitosi | 43/111 |
| 3,956,848 A * | 5/1976 | Job | 43/115 |
| 5,646,404 A | 7/1997 | Litzkow et al. | |
| 5,711,953 A * | 1/1998 | Bassett | 424/405 |
| 5,737,870 A | 4/1998 | Thind | |
| 5,813,166 A | 9/1998 | Wigton et al. | |
| 5,939,062 A * | 8/1999 | Heath et al. | 424/84 |
| 6,083,498 A * | 7/2000 | Landolt | 424/84 |
| 6,190,653 B1 | 2/2001 | Landolt et al. | |
| 6,585,991 B1 | 7/2003 | Rojas et al. | |
| 6,662,489 B2 | 12/2003 | Spiro et al. | |
| 6,707,384 B1 * | 3/2004 | Shuman et al. | 340/573.2 |
| 6,843,985 B2 * | 1/2005 | Erickson, Jr. et al. | 424/84 |

(Continued)

FOREIGN PATENT DOCUMENTS

JP    7289137 A    11/1995

(Continued)

OTHER PUBLICATIONS

"Trapping of the malaria vector Anopheles gambiae with odour-baited MM-X in semi-field conditions in western Kenya"; Njiru, B., et al., Malaria Journal, Biomed Central, London, GB; vol. 5, No. 1, May 15, 2006; pp. 39-46; XP021017910.

(Continued)

*Primary Examiner* — David A. Rogers

(57) ABSTRACT

Methods determine how effective a product that dispenses an insect repellent or insecticide is in controlling flying insects such as mosquitoes, with no or reduced need for human test subjects. An insect trap or other automated monitoring device is positioned in a test environment and operated in a manner so as to mimic some human attribute (e.g. by dispensing carbon dioxide). Trap/monitoring results in the presence and absence of the operating product are obtained in order to judge relative effectiveness of the active. Further, the real time evaluation of insect populations permits evaluation of time needed to achieve base effectiveness and length of time that effectiveness can be sustained.

9 Claims, 5 Drawing Sheets

U.S. PATENT DOCUMENTS

| | | |
|---|---|---|
| 6,882,279 B2 | 4/2005 | Shuman et al. |
| 6,899,280 B2 * | 5/2005 | Kotary et al. .................. 239/34 |
| 6,920,716 B2 | 7/2005 | Kollars, Jr. et al. |
| 7,275,499 B2 | 10/2007 | Palomino et al. |
| 7,401,436 B2 * | 7/2008 | Chyun ............................ 43/113 |
| 2002/0144452 A1 | 10/2002 | Beroza |
| 2002/0185605 A1 * | 12/2002 | Shuman et al. ............ 250/341.7 |
| 2005/0031661 A1 * | 2/2005 | Landolt et al. ................ 424/405 |
| 2005/0090560 A1 * | 4/2005 | Erickson et al. ............. 514/675 |
| 2005/0091911 A1 * | 5/2005 | Matts et al. .................... 43/131 |
| 2005/0223625 A1 | 10/2005 | Whitlow et al. |
| 2005/0274061 A1 | 12/2005 | Zhu |
| 2005/0279016 A1 * | 12/2005 | Williams et al. ............... 43/122 |
| 2006/0067965 A1 * | 3/2006 | Chandra et al. ............. 424/405 |
| 2006/0147562 A1 * | 7/2006 | Sommerville ............... 424/736 |
| 2006/0179708 A1 * | 8/2006 | Garland ......................... 43/107 |
| 2007/0124988 A1 | 6/2007 | Spiro et al. |
| 2007/0154504 A1 | 7/2007 | Coats et al. |
| 2009/0094883 A1 * | 4/2009 | Child .............................. 43/112 |

FOREIGN PATENT DOCUMENTS

| | | |
|---|---|---|
| JP | 2000135043 A | 5/2000 |
| JP | 2001017054 A | 1/2001 |
| WO | 95/29585 A | 11/1995 |
| WO | 00/19820 A | 4/2000 |
| WO | 03/094611 A | 11/2003 |

OTHER PUBLICATIONS

Database WPI Week 199604; Thomson Scientific, London, GB; AN 1996-035073; XP002523454.

Database WPI Week 200034; Thomson Scientific, London, GB; AN 2000-393666; XP002523455.

Database WPI Week 200120; Thomson Scientific, London, GB; AN 2001-197093; XP 002523456.

PCT/US2008/004955 International Search Report and Written Opinion dated Apr. 24, 2009 (J-4823A).

A web site excerpt, admitted prior art, depicting a Model 912 trap marketed by John W. Hock Company, (Oct. 2004).

B. Collier et al., Field Evaluation Of Mosquito Control Devices In Southern Louisiana, 22 J. Am. Mosquito Control Assoc. 444-450 (2006).

* cited by examiner

| PERCENT REPELLENCY* | | | | |
|---|---|---|---|---|
| | CITRONELLA CANDLE | | THERMACELL® | |
| | TRAP% REDUCTION | REP AVERAGE | TRAP% REDUCTION | REP AVERAGE |
| REP 1 | 0 | | 81 | |
| | 0 | | 92 | |
| | 0 | 0 | 89 | 88 |
| REP 2 | 0 | | 86 | |
| | 0 | | 69 | |
| | 0 | 0 | 89 | 83 |
| REP 3 | 70 | | 97 | |
| | 72 | | 81 | |
| | 83 | 76 | 93 | 91 |
| | | | | |
| AVERAGE | | 25 | | 87 |

| PERCENT REPELLENCY* |||||
|---|---|---|---|---|
| | CITRONELLA CANDLE || OFF! LAMP ||
| | TRAP% REDUCTION | REP AVERAGE | TRAP% REDUCTION | REP AVERAGE |
| REP 1 | 0 | | 81 | |
| | 0 | | 89 | |
| | 0 | 0 | 82 | 84 |
| REP 2 | 0 | | 96 | |
| | 0 | | 91 | |
| | 0 | 0 | 89 | 92 |
| REP 3 | 55 | | 94 | |
| | 89 | | 97 | |
| | 75 | 75 | 95 | 96 |
| AVERAGE | | 25 | | 91 |

FIG. 5

PERCENT REPELLENCY PER REPLICATION

| | CITRONELLA CANDLE | THERMACELL® |
|---|---|---|
| REP 1 | 56 | 66 |
| REP 2 | 79 | 90 |
| REP 3 | 0 | 84 |
| REP 4 | 37 | 92 |
| REP 5 | 69 | 79 |
| REP 6 | 50 | 53 |
| REP 7 | 78 | 67 |
| REP 8 | 77 | 87 |
| AVERAGE % REPELLENCY* | 56a | 77a |

FIG. 6

PERCENT REPELLENCY

| CITRONELLA CANDLE | | THERMACELL® | |
|---|---|---|---|
| REP 1 POSITION A | 54.64% | REP 1 POSITION A | 85.79% |
| REP 1 POSITION B | 55.71% | REP 1 POSITION B | 84.76% |
| REP 1 POSITION C | 64.98% | REP 1 POSITION C | 88.81% |
| | | | |
| AVG. % REPELLENCY REP 1 | 59.25% | AVG. % REPELLENCY REP 1 | 86.72% |
| | | | |
| REP 2 POSITION A | 0% | REP 2 POSITION A | 0.00% |
| REP 2 POSITION B | 38.99% | REP 2 POSITION B | 52.83% |
| REP 2 POSITION C | 0% | REP 2 POSITION C | 78.26 |
| | | | |
| AVG. % REPELLENCY REP 2 | 13% | AVG. % REPELLENCY REP 2 | 49% |

FIG. 7

METHODS FOR TESTING INSECT CONTROL PRODUCTS

CROSS-REFERENCE TO RELATED APPLICATIONS

This application claims priority based on U.S. provisional application 60/913,333 filed on Apr. 23, 2007.

STATEMENT REGARDING FEDERALLY SPONSORED RESEARCH/DEVELOPMENT

Not applicable.

BACKGROUND OF THE INVENTION

The present invention relates to methods for evaluating the effectiveness of volatile insect control chemicals, such as insect repellents and insecticides. "Insect control" is defined as including the repelling, killing, rendering inactive, or otherwise affecting the behavior of insects or of other arthropods commonly controlled with insects. More particularly, the invention relates to the use of traps and other insect monitoring devices to test the effectiveness of various chemicals (sometimes referred to herein as "actives" or "active ingredients"), chemical delivery systems, and concentrations, while reducing the need to expose humans to the risk of being bitten during such efficacy experiments.

Various devices such as mosquito coils, heatable impregnated mats, heatable wick-type dispensers, burnable candles, and other dispensers of insect control actives disperse insect control actives into the air. Some require externally applied heat or applied blown air, while others do not. For purposes of the present application, all volatile delivery devices are being referred to, except as expressly stated, and will sometimes be referred to simply as the "products."

In the course of developing such products, tests involving human test subjects have traditionally been used in order to guide efforts to optimize concentrations, heating conditions, air flow conditions, and other factors. For example, human test subjects have been positioned in a test area and exposed to the volatile insect control active ingredients delivered by a product and potentially also to biting insects such as mosquitoes or flies. The human test subjects have typically stayed in the test area for a set period while the degree of insect activity was observed, including insect lands on the human test subjects and even possible biting.

This process sometimes exposes human test subjects to higher levels of active than are later determined necessary for protection, it requires human test subjects to be willing to be exposed to insect activity and even biting, and it requires compliance with environmental and ethical protocols relating to human testing. Further, such testing requires obtaining enough human test subjects to establish statistical assurance. Moreover, insects respond differently to different individual human subjects, particularly when they have significantly different body temperatures, odors, and/or rates of emission of carbon dioxide introducing difficult to quantify variables from test to test.

A wide variety of insect traps are known, including some primarily intended for trapping mosquitoes and/or other flying insects. A well-known mosquito trap is the Center For Disease Control trap #912 which generates carbon dioxide as an attractant for mosquitoes. Center For Disease Control trap #512 is very similar to trap #912 and can be used in much the same way as the #912 trap. Although both of those traps are capable of generating carbon dioxide, it is also possible and may be operationally preferable to dispense carbon dioxide via the traps but drawn from a tank or other separate source. See generally FIG. 1.

In U.S. Pat. No. 7,275,499 there was discussion of using a cork impregnated with a repellent to partially test the effectiveness of the repellent by viewing how long mosquitoes stayed away from the corks that were so treated. However, this test system was not well suited to take into account a variety of other variables (e.g. adjustments to the dispensing product).

U.S. patent application publication 2007/0154504 proposed testing repellent effectiveness using a Petrie dish holding a repellent reservoir, and observing how long an insect stayed near the chemical. This only evaluated a limited range of characteristics, and in any event is an awkward technique with respect to flying insects as distinguished from cockroaches.

U.S. Pat. No. 6,585,991 disclosed that an array of baits and attractants could be positioned in an area for monitoring termite presence.

In B. Collier et al., Field Evaluation Of Mosquito Control Devices In Southern Louisiana, 22 J. Am. Mosquito Control Assoc. 444-450 (2006) there was a description of using a trap that generated carbon dioxide to test the effectiveness of various insect control devices in suppressing insect populations. However, the test systems described therein were not suitable for precisely measuring certain parameters of effectiveness, such as how soon the product becomes effective, how long it remains effective, and what it is effective against over varying time periods.

In unrelated work, there have been a variety of attempts, primarily by the United States Department Of Agriculture, to provide various devices to analyze the number and type of insects falling past a monitoring point (e.g. using infrared or other counting devices). These systems were primarily intended to monitor infestation in stored grains or the like. See e.g. U.S. Pat. Nos. 5,646,404, 6,707,384 and 6,882,279.

As such, there is still a need for improved methods for efficacy testing of insect control products which minimize the need for human subjects, yet evaluate a wide variety of device and use condition factors.

BRIEF SUMMARY OF THE INVENTION

In one aspect the invention provides a method for evaluating effectiveness of a product that dispenses an insect control active in controlling a selected population of insects. One obtains an insect trap and places it in a test environment where the test environment contains the selected population of insects. The insect trap has an automated monitor for automatically monitoring and reporting the entry of insects into the trap.

One then determines an extent to which, in the test environment during a control period, insects enter in the insect trap when the environment is essentially free of the insect control active, separately determines an extent to which, in the test environment during a test period, insects enter in the insect trap when the environment has the insect control active dispensed into it by the product, and then compares determined results regarding such entering during the control and test periods. One then estimates using this comparison an extent to which operation of the product can control the insect population.

In preferred forms the automated monitor is in the form of a counter that can count insects entering the trap during a defined period, most preferably where the counter can also exclude items from the counting that are outside of a defined size range. The insect control active can be a repellent, an insecticide, or other insect control active. The test environment may be an outdoor site, or an inside site such as an enclosed test chamber or an interior room. For example, the insects could be mosquitoes and the method could help estimate the degree to which the product can inhibit the mosquitoes from biting humans.

The trap should preferably have one or more attractants which mimic naturally occurring human attractants (e.g. highly preferably a source of carbon dioxide). It is also preferred to have a trap that traps insects by sucking adjacent insects into a region of the trap that retains the insects, past a monitor that detects insects being sucked into the trap.

One possible monitor is an infrared monitor such as those disclosed in U.S. Pat. No. 5,646,404 or U.S. Pat. No. 6,882,279 (the disclosure of which is hereby incorporated by reference as if fully set forth herein). Alternatively, laser counter systems analogous to those used in pill counting systems may be adapted for use with the traps of the present invention. One suitable laser counter system is available from Baumer Ltd., of Southington, Conn. as Baumer's model ZADM 034P240.6921 line sensor. In any event, to provide increased information about spatial effectiveness, it is desired that multiple such traps be positioned in the test environment simultaneously during the method at at least three different locations.

Also, to better calibrate results, it is desirable to also have the method conducted on two different products having a previously known relative effectiveness when compared to each other so as to be able to estimate how differences in monitoring results correlate to differences in relative effectiveness. If, for example, one knows from other testing that one product is twice as effective as the other, and one sees a fourfold monitoring change in such an experiment, one will be able to better correlate the extent of monitoring feedback differences with the extent of effectiveness differences in other experiments.

In another aspect the invention provides a method for evaluating effectiveness of a product that dispenses an insect control active in controlling a selected population of insects. One obtains an insect monitoring device and places it in a test environment where the test environment contains the selected population of insects, wherein the insect monitoring device has an automated monitor for automatically monitoring and reporting regarding insects entering the monitoring device.

Note that here the device could simply be a window passage that counts without trapping. While this provides some information, it is not as preferred as it does not allow one to examine a "catch" to confirm exactly which types of insects are being affected.

In any event, in this alternative method one determines an extent to which, in the test environment during a control period, insects enter in the insect monitoring device when the environment is essentially free of the insect control active, determines an extent to which, in the test environment during a test period, insects enter in the insect monitoring device when the environment has the insect control active dispensed into it by the product, and then compares determined results regarding such entering during the control and test periods. One then estimates, using this comparison, an extent to which operation of the product can control the insect population.

The desired "control" effect is typically insect knockdown, repelling or killing sufficient for the insects to be kept enough away from the trap to avoid entering (and hence away from a human). An insect is "knocked down" when it is rendered inactive, whether or not actually dead.

Preferably, the trap(s) or other monitoring devices are allowed to trap/monitor the target insects for an initial period of time before the product is introduced or activated so as to measure the insect pressure at the test site as a negative control. Then, the product is allowed to operate, and the trap/monitor rate of the target insect is observed. Preferably, each entering activity is noted at successive times throughout the time the test is allowed to run so as to observe the effect of the product over time.

Automated devices are available commercially for preserving trapped insects in separate, successive containers, thus allowing a test to run without any complication from the periodic disruption of the site by the presence of a human coming to monitor the "harvest" in the traps. The species collected at various times can then be later reviewed to evaluate species effects, and the general effectiveness of a product as it might vary over time can be observed.

If the test site is outdoors or in any location subject to wind or air movement, it is most preferred that at least one trap be located downwind of the product location. Preferably at least three traps are used overall, arranged so as to be spaced from the product and to be evenly radially distributed around the product. In some test situations, it is also preferred to have a multiplicity of traps located at increasing distances from the product location so as to determine the reach of the product's effects.

By use of the methods of the invention, insect control dispensing products can be tested without the need to expose humans to the active being dispensed or to insects (or other conditions of the testing site). Furthermore, testing can readily be accomplished in outdoor, household, test chamber, or other locations, and such testing can be conducted without employing equipment that could itself introduce interfering variables into the test location.

Moreover, and perhaps most importantly, one can evaluate how quickly adequate protection can be achieved at various distances, and how long adequate protection lasts, at various spatial distances. This can be evaluated while also considering which specific species are controlled. This information can then be used in a feedback/development way to optimize the product itself.

These and still other advantages of the present invention will be apparent from the description which follows and the accompanying drawings. In them reference is made to certain preferred example embodiments. However, the claims should be looked to in order to judge the full scope of the invention, and the claims are not to be limited to just the preferred example embodiments.

BRIEF DESCRIPTION OF THE DRAWINGS

FIG. 5 is a table reporting on experiments comparing a citronella candle with an OFF!® lamp;

FIG. 6 is a table reporting on another set of experiments comparing a citronella candle with a ThermaCell® device; and FIG. 7 is a table reporting on yet another set of comparative experiments comparing a citronella candle with a ThermaCell® device.

DETAILED DESCRIPTION OF THE PREFERRED EMBODIMENTS

Figure 1:
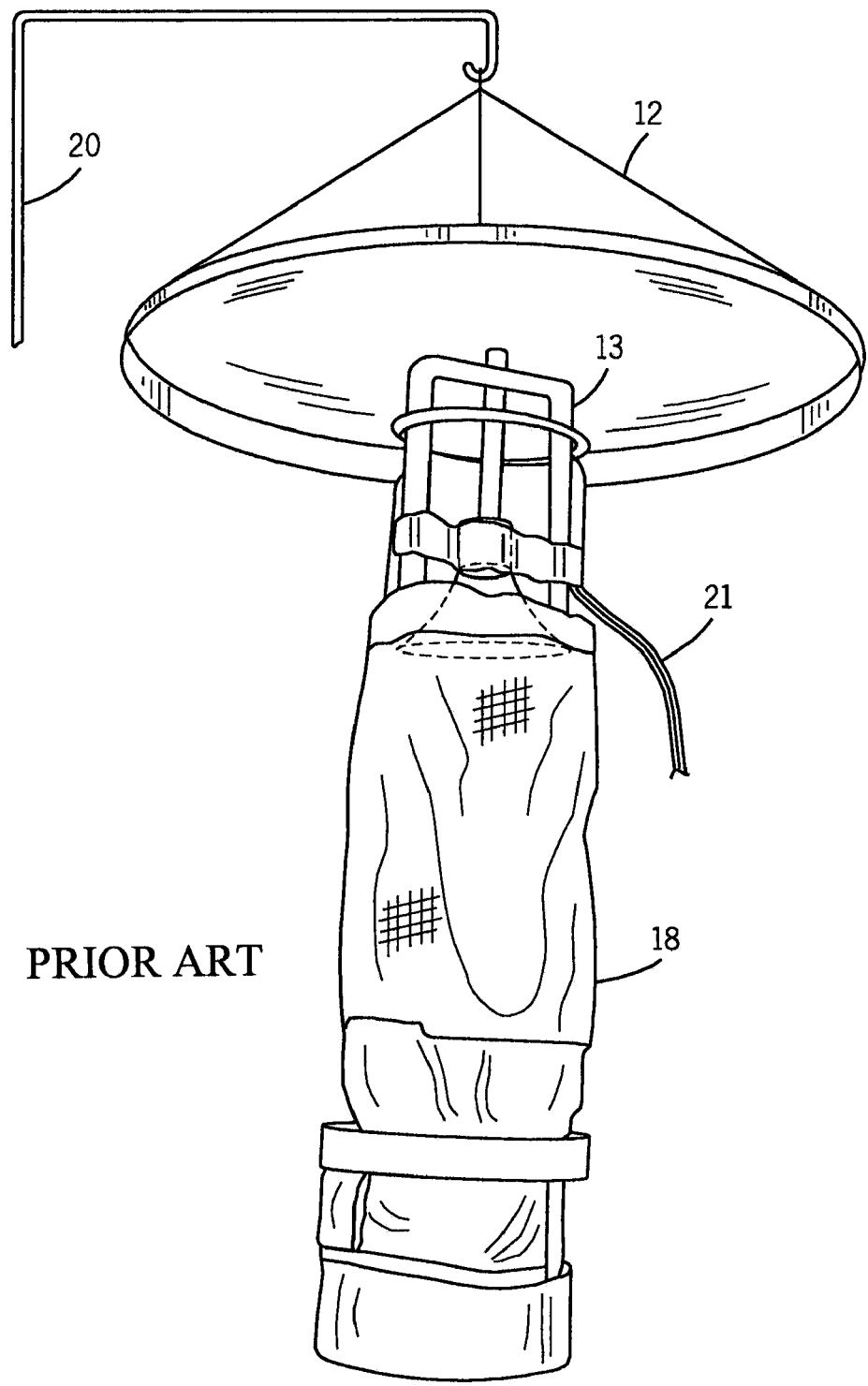
FIG. 1 is a frontal perspective view of a trap suitable for use with the methods of the present invention.

Methods of the present invention employ traps for flying insects to successively sample insect populations as they are affected by the operation of an insect control product. An insect of special interest is the mosquito, for which the preferred traps are mosquito traps that use attractants such $CO_2$, octanol, lactic acid, heat, humidity, or other known attractants to draw mosquitoes towards the trap. Preferably the attractant mimics to some extent an attractant naturally generated by a human, such as $CO_2$ generation. Light can also be used as an attractant, albeit this also tends to attract a variety of other flying insects, making counting more difficult.

Trap collection and/or monitoring mechanisms are varied. As one example, traps may be used which employ a fan-driven suction arrangement to force closely adjacent mosquitoes into catch bags or bottles or onto sticky paper.

Where traps employing $CO_2$ attractants are used, they can be set at a $CO_2$ release rate per minute similar to the $CO_2$ output of the average human being. $CO_2$ can be delivered from gas tanks, but alternatively could be generated via burning of propane or other fuel, or via other techniques. CDC #512 traps are preferred, modified with a monitor as described herein, although the more expensive CDC #912 traps are also suitable. Each of those two traps is also equipped with a light source. When testing for mosquito or fly response, it is preferred to inactivate the light source in order to avoid also attracting moths and other light-responding insects.

The catch bags or bottles, sticky paper, or other retention arrangement for each trap can periodically be changed during a test period to monitor collection at various times across the test period. The use of a mechanical bag or bottle changer that automatically changes bags or bottles at set times during the test can also be employed.

Multiple traps can be placed around the area in which a test is to be conducted at pre-selected distances from a product to be tested. Traps are most preferably placed in the trending downwind direction when the test is outdoors.

Ideally, at least 3 traps should be placed around the product (see FIG. 3), including the upwind direction. While optimal efficacy of area or spatial repellent products is observed downwind from the product, monitoring of the entire area is important. Winds periodically shift over test periods. Surrounding the product being tested with traps avoids the need to repeatedly move traps to maintain trapping in the downwind direction.

Multiple test plots within an overall test area can be evaluated for each test to provide greater statistical assurance. An untreated control is desirable both for monitoring mosquito populations throughout the test and for calculating percent reduction in the treated areas. Prior to treatment (placing the product in the test site), pre-counts should be taken in each test plot to determine the variability in population between each plot. These numbers will be applied to the formula for calculating percent reduction.

Multiple replications should be conducted for each test, again to improve statistical assurance. Ideally, a commercialized active of known efficacy is included in the test as a second, positive control.

Prophetic Example 1

Figure 2:
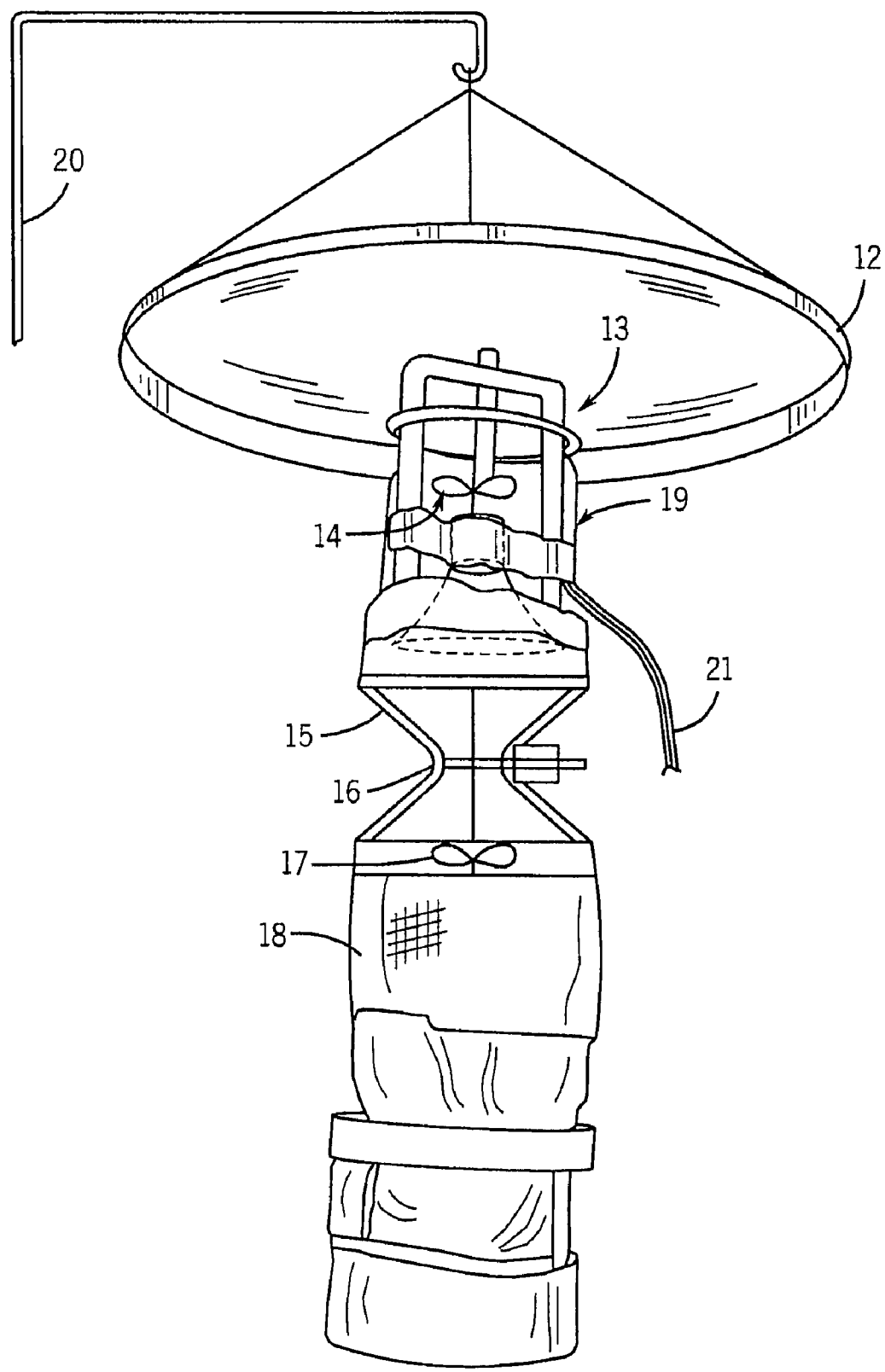
FIG. 2 is a view similar to FIG. 1, but of an alternative trap modified in accordance with the present invention to provide a monitoring system.

The following is an example application of the method to test the efficacy of mosquito repellent products. One can use CDC #912 traps (modified as shown in FIG. 2) with a $CO_2$ emission rate set to deliver approximately 500 ml/min.

In this regard, there can be an upper shield 12 over an entry 13 in which there is a first fan 14 that then sucks insects past a constriction 15 where there is mounted an infrared monitor or laser monitor 16. The insects then continue to fall and be drawn downward with the assistance of second fan 17 into the collector bag 18. Preferably, there is a plastic cylinder 19 around the entry 13 to help minimize the disturbing effects of fan 14 on the environment. Conduits 21 can provide the $CO_2$ source and/or power to the fans. It is also preferred to use tables, poles 20, or other structures to hold test products in a manner corresponding to their intended use.

When appropriate in light of the expected use of the product to be tested, outdoor test sites are selected so as to ensure the presence of mosquitoes due to natural presence and to test under actual expected use conditions, although, in other situations, an interior room or a test chamber with introduced mosquitoes may be appropriate. Assuming for this example that an outdoor test site is available and appropriate, the test site should be large enough to provide for the defining of multiple, 15.25 m by 15.25 m test plots with an approximate 15.25 m buffer zone between the plots.

Mosquito traps are set up in various areas of the test site and are allowed to collect mosquitoes to verify the adequacy of the site and the base level of trap results (the negative control). This should be done at a time of day and under other conditions similar to those that are expected to be present when the product test is subsequently to be conducted. It is preferred to test under conditions such that a catch rate of at least 60 mosquitoes per hour is observed before starting product evaluation. Of course, if such test sites exhibiting such catch rates are not available, collection times can be lengthened to increase overall catch size.

Once an adequate catch rate is observed, verifying the adequacy of the test site, multiple test plots should be designated, preferably having the size, shape, and spacing indicated, above. The plots should be arrayed roughly in a line extending perpendicular to the trending wind direction so as to minimize any possible overflow of dispensed active ingredient from one plot to the next.

Unless a test product is to be placed directly on the ground (in which case reference hereafter to the product holder will be understood to simply be the ground location where the test product will be placed), a product holder is set up in the middle of each test plot. The product holder is designed to hold the test product at a height and in a manner corresponding to the intended end use of the product. Typically, a table, pole, or other product holder approximately 0.6-0.9 m high is adequate.

At least three and preferably four or more mosquito traps are spaced around the middle of each test plot at a selected, measured distance from the product holder, the distance being selected as that at which the efficacy of the test product is to be evaluated. Preferably, the traps are spaced evenly around the product holder so that, for example, if three traps are used, they are separated from each other by angles of 120 degrees (or 90 degrees if four traps are used, etc.). Preferably, at least one trap is located substantially down-wind of the product holder. If desired, more than one array of such traps can be used, set at increasing distances from the product holder.

The trending wind direction is determined using direction flags or smoking sticks to insure that a trap is correctly located substantially down-wind of the product holder. Periodically the wind speed and direction are recorded. Preferably, temperature, relative humidity, or other environmental variables capable of affecting mosquito activity, product performance, or other factors that could affect test results are also periodically recorded throughout test. Collection bags (to hold mosquitoes) are attached to the mosquito traps, with the traps' $CO_2$ flow rate adjusted to be similar to the $CO_2$ production of an average human.

Once the test site is set up, the traps' $CO_2$ flow is activated and the traps are allowed to collect mosquitoes for a selected, pre-count collection period, preferably of 1 hour (or more, if an only modest mosquito population requires a longer period for a useful collection). At the end of the precount collection period, the collection bags are removed and preserved for later examination. New, empty bags are attached.

Next, a test product is placed in each test site, except that at least one test site is preserved as an untreated area to serve as a control. The test products are activated, and the traps are allowed to collect mosquitoes for the collection period used for the pre-count collection. Then bags are collected and preserved for later examination and replaced with new bags, with this process being repeated for the number of times desired, whether to simply provide replicated tests or to observe the effect of the test product over time.

A sample of mosquitoes from the pre-count catch is examined and preferably identified by genus and, even more preferably, by species to determine types of mosquitoes in the test system. The mosquitoes in all pre-count and treatment count phase catch bags are counted. If the effect of the test product on specific types of mosquitoes is deemed important, the treatment count catch bags are also examined by genus or species.

Percent repellency is calculated for each individual count using the following formula:
C1=pre-count of control
C2=control count at time corresponding with treatment count
T1=pre-count for treatment area
T2=treatment area count at designated time
Hence, $(1-((C1 \times T2)/(T1 \times C2)) \times 100$=Percent repellency. Percent repellencies for each count are averaged and standard deviations calculated. Further statistical analysis can be conducted, if desired.

Preferably, full balanced block experiments should be designed for this type of testing to insure that each test variable is tested in each location. Thus, with the same traps remaining in each test plot, alternative test products can be rotated through the test plots. A negative control, such as citronella candles, in addition to the untreated control, should be considered in each set of tests. A high number of replicates is desirable to insure consistency in the data.

Example 2

The procedure of Example 1 was followed in Example 2, except as expressly noted. To minimize the number of non-target insects collected, the trap lights were turned off for the duration of the test. Traps were hung from about 1.5 m poles. The tested active was ThermaCELL® mosquito repellent device, EPA Reg. #71910-2. The ThermaCELL® device is a portable butane heater that heats a tray on which is placed an active-impregnated, cellulosic tablet of the sort commonly referred to as a "mosquito mat." The heat delivers volatile active from the mosquito mat. In alternative experiments, the tested active was 21.97% d-cis/trans allethrin as dispensed from a Raid® Protector Outdoor Mozzie Lamp (an Australian product sold by S. C. Johnson & Son, Inc. that is identical to the United States product sold by S. C. Johnson & Son, Inc. as the "Off!® Mosquito Lamp," EPA Reg. #4822-469). In the discussion, below, and elsewhere herein, the lamp used will be referred to simply as the "Off!® Lamp." The Off!® Lamp uses heat from a candle to volatilize active from a mosquito mat.

One negative control was a citronella candle. Another negative control dispensed no active. The test site was located adjacent to a mangrove swamp. The test site consisted of a long rectangular area approximately 122×24.4 m. Winds tended to flow perpendicular to the 122 m side. The test site was split into three equal plots, each approximately 39.6 m by 24.4 m. The center of each plot was marked for eventual placement of the test samples.

In pretesting, mosquito populations were observed to be moderate, achieving a capture rate in the traps of about one mosquito per minute in each trap. The pre-count and treatment counts each lasted for 2.5 hours. The average catch per test plot during the pre-count (three traps cumulative) was 246.

A variety of mosquitoes were trapped including *Culex annulirostris, Culex sitiens, Aedes kochii, Aedes vigilax* (salt-marsh mozzi, most similar to *taeniorhynchus*), *Aedes notoscriptus* (domestic container breeder), *Aedes lineatopennis, Aedes trmulus, Aedes alternans, Verralina carmenti, Anopheles farauti*—(malaria-transmitting mosquito), *Mansonia uniformis* and *Aedes aegypti*.

Figures 3, 4:
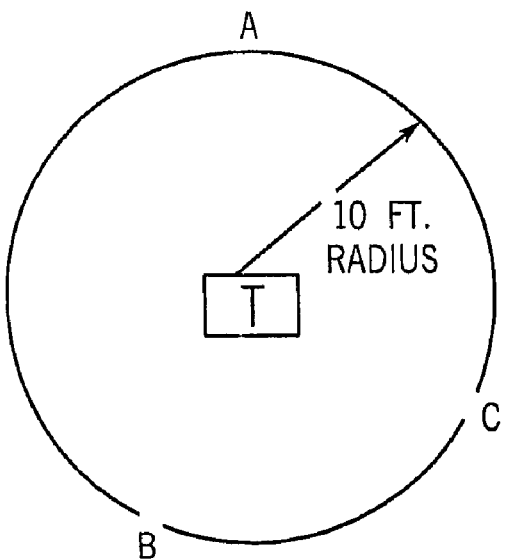
FIG. 3 is a schematic top view depiction of how an insect control dispenser product "T" can be positioned within an array (A, B, C) of multiple traps in accordance with the present invention.
FIG. 4 is a table comparing experimental results of tests of the effectiveness of a citronella candle with a ThermaCell® dispenser.

Three traps were placed in each test plot. The center of each test plot served as the vertex of a 6.1 m diameter (3.05 m radius, area of 29 sq. meters) circle. As shown in FIG. 3, traps (A, B, C) were placed around the circumference of the circle (3.05 m from center) at every 120 degrees. Test products, also referred to herein as "test samples" ("TS"), were placed in the middle of the circle.

Initial testing verified the desirability of having a pre-count to establish relative mosquito catch numbers for each test plot for comparison purposes with the treatment catches. Three test plots were set-up as depicted in the FIG. 3 drawing. At the start of each test, catch bags were attached to mosquito traps, trap fans were turned on, and $CO_2$ flow was started, regulated at 500 ml/min. Traps were allowed to catch for 2.5 hours. After 2.5 hours, catch bags were collected and replaced with new bags.

Directly after the pre-counts, one plot was randomly selected for the ThermaCELL® repellent device. The ThermaCELL® repellent mat was placed on the heating tray, and the butane heater was activated. The ThermaCELL® product was then placed on a tray table at a height of about 1 m in the middle of the circle. The second plot was randomly selected for the citronella candle treatment. Two citronella candles were placed on the ground in the middle of that plot's circle. No treatment was placed in the third plot designated as the untreated control. After samples were placed, traps were allowed to catch mosquitoes for an additional 2.5 hours. At the end of the 2.5 hours, catch bags were collected and test samples were turned off (or, with respect to the candles, flame extinguished).

Testing was conducted over three nights with each test sample variable being tested once in each of the three test plots (3×3 balanced block experimental design). Test traps remained in same positions at all times to insure that each trap was allowed to participate in catching for all three test sample variables.

For each treatment and each replicate, pre-counts were compared to treatment counts to calculate Percent Reduction. The following formula was used:

$$(1-((C1 \times T2)/(T1 \times C2)) \times 100 = \text{Percent Reduction}$$

a. C1=pre-count of control
b. C2=control count at time corresponding with treatment count
c. T1=pre-count for test area
d. T2=test area count at designated time Replicates were then averaged for each treatment.

FIG. 4 is a chart showing the percent reduction for citronella candles and ThermaCELL® area repellent. As was expected, the citronella candles had a much poorer performance. Importantly, this confirmation of the test methods was achieved without requiring a human test subject to be exposed to insect biting. In this regard, the ThermaCELL® device had been previously successfully tested with human test subjects several years before the test described here.

Next a comparison was made between citronella candle performance and that of the Off!® Lamp. The exact same experimental set-up was used, except that the Off!® Lamp was substituted for the ThermaCELL® product. The focus of this testing was to determine whether another repellent of known efficacy was shown to be able to consistently repel mosquitoes from a defined area (roughly a 6.1 m diameter circle).

The FIG. 5 chart shows the percent catch reduction (treated as percent repellency) for citronella candles and Off!® Lamp. Again, it was determined that a dispensing product worked better than a citronella candle without using human test subjects.

A comparison was then made between the results of the testing using this system against the results achieved using human test subjects over the past decade. For example, a considerable amount of testing had been conducted during the development of the Off!® Lamp, using human test subjects, and in that testing, the overall average percent reduction over four hours of testing (15 replicates) was about 84%. Under slightly different test conditions, and using the present test system, an average of 91% reduction was calculated. A correlation was therefore demonstrated between human testing and the testing method of the invention. Further, it is believed that as the attractant used (e.g. odor, heat, gas, moisture) more completely mimics average humans, the correlation will become even stronger.

It is noted that the citronella candles performed poorly, as expected, in 4 of 6 replicates. However, two replicates showed a 75% reduction. Variability in test populations appears to have caused this increase in percent reduction. Hence, it is advisable to conduct 10 or more replicates to increase the sample size and obtain greater statistical certainty.

While the above experiments were under preferred conditions, a number of other experiments had been conducted whose results are the subject of FIGS. 6 and 7. Using the information from these preliminary experiments, the test protocol was refined as noted above.

After these initial experiments, the use of an automated counter was introduced, the use of the counter permitting more refined analysis. One can track when in a given day period the insect harvest is at a high level, and when it is not, relative to controls. This provides information as to how quickly the product being tested becomes effective, at what distances, for how long, and for what species. It should be appreciated that this type of precise information helps optimize the product itself, and then helps tailor information to the consumer regarding how the product is to be used for specific effectiveness.

While the above describes a number of preferred example embodiments of the present invention, other embodiments are also within the scope of the invention. For example, the present invention is useful to test control of other flying insects such as house flies.

Further, while particular devices and actives dispensed thereby have been tested, the principles of the present invention should be applicable to a wide variety of other types of dispensing devices (e.g. burnables such as mosquito coils; heatable substrates; fan blown systems), and a wide variety of insect control active ingredients useful against flying or other insects. Thus, the claims that follow should be looked to in order to judge the full scope of the invention.

INDUSTRIAL APPLICABILITY

The present invention provides methods for testing air dispersible actives (such as insect control agents) without requiring human test subjects.

What is claimed is:

1. A method for evaluating effectiveness of a dispensing product that dispenses from the dispensing product an insect control agent selected from the group consisting of insect repellents and insecticides, in controlling a selected population of insects in an environment, comprising the steps of:
   obtaining an insect trap and placing it in the environment where the environment comprises the selected population of insects, wherein the insect trap has an automated monitor for automatically monitoring and reporting the entry of insects into the trap;
   determining an extent to which, in the environment during a control period, insects enter the insect trap when the environment is essentially free of the insect control agent;
   determining an extent to which, in the environment during a test period, insects enter the insect trap when the environment outside of the trap has had the insect control agent dispensed into it by the dispensing product;
   comparing determined results regarding such entering during the control and test period; and
   then estimating using this comparison an extent to which operation of the dispensing product can control the insect population;
   where multiple such traps are positioned in the environment surrounding the dispensing product simultaneously during the method at least three different locations.

2. The method of claim 1, wherein the automated counter can estimate how many insects enter the trap during a defined period.

3. The method of claim 1, wherein the automated counter can estimate how many insects of a defined size range enter the trap during a defined period.

4. The method of claim 1, wherein the environment is an outdoor site.

5. The method of claim 1, wherein the environment is one of an interior room and an enclosed test chamber.

6. The method of claim 1, wherein the insects are mosquitoes and the method helps estimate a degree to which the product can inhibit the mosquitoes from biting humans.

7. The method of claim 1, wherein the insect trap expels carbon dioxide as an attractant.

8. The method of claim 7, wherein the insect trap traps insects by sucking adjacent insects into a region of the trap that retains the insects.

9. A method for evaluating effectiveness of a dispensing product that dispenses from the dispensing product an insect control agent selected from the group consisting of insect repellents and insecticides, in controlling a selected population of insects in an environment, comprising the steps of:

obtaining an insect trap and placing it in the environment where the environment comprises the selected population of insects, wherein the insect trap has an automated monitor for automatically monitoring and reporting the entry of insects into the trap;

determining an extent to which, in the environment during a control period, insects enter the insect trap when the environment is essentially free of the insect control agent;

determining an extent to which, in the environment during a test period, insects enter the insect trap when the environment outside of the trap has had the insect control agent dispensed into it by the dispensing product;

comparing determined results regarding such entering during the control and test period; and then estimating using this comparison an extent to which operation of the dispensing product can control the insect population;

wherein the method is conducted on at least two different dispensing products having a previously known relative insect control effectiveness when compared to each other so as to be able to thereafter estimate how differences in trapping results correlate to differences in relative effectiveness of insect control.

* * * * *

UNITED STATES PATENT AND TRADEMARK OFFICE
CERTIFICATE OF CORRECTION

PATENT NO. : 7,921,594 B2
APPLICATION NO. : 12/032834
DATED : April 12, 2011
INVENTOR(S) : Daniel T. Ropiak et al.

Page 1 of 1

It is certified that error appears in the above-identified patent and that said Letters Patent is hereby corrected as shown below:

Column 10, Line 51: insert --at-- after "method at"

Signed and Sealed this
Sixth Day of September, 2011

David J. Kappos
*Director of the United States Patent and Trademark Office*